(12) United States Patent
Kishishita et al.

(10) Patent No.: US 6,790,470 B1
(45) Date of Patent: Sep. 14, 2004

(54) ASPARTAME DERIVATIVE CRYSTAL AND PROCESS FOR PRODUCING THE SAME

(75) Inventors: Akihiro Kishishita, Kawasaki (JP); Kazutaka Nagashima, Kawasaki (JP); Hirotoshi Ishida, Kawasaki (JP); Takeshi Nagai, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/708,006

(22) Filed: Nov. 8, 2000

Related U.S. Application Data

(63) Continuation of application No. PCT/JP99/02199, filed on Apr. 26, 1999.

(30) Foreign Application Priority Data

| May 8, 1998 | (JP) | .......................................... | 10-125991 |
| Jul. 23, 1998 | (JP) | .......................................... | 10-207605 |

(51) Int. Cl.⁷ ........................ A23L 1/236; C07C 229/00
(52) U.S. Cl. ........................................ 426/548; 560/40
(58) Field of Search ........................... 426/548; 560/40, 560/41

(56) References Cited

U.S. PATENT DOCUMENTS

| 4,579,747 A | * | 4/1986 | Sugiyama et al. |
| 4,810,818 A | * | 3/1989 | Wakamatsu et al. |
| 5,480,668 A | * | 1/1996 | Nofre et al. |
| 5,510,508 A |   | 4/1996 | Claude et al. |

FOREIGN PATENT DOCUMENTS

| JP | 59-172444 | 9/1984 |
| JP | 60-37949  | 2/1985 |
| JP | 63-33396  | 2/1988 |
| JP | 63-44592  | 2/1988 |
| JP | 63-177774 | 7/1988 |
| JP | 2-243699  | 9/1990 |
| JP | 3-27398   | 2/1991 |
| JP | 3-204895  | 9/1991 |
| JP | 4-346769  | 12/1992 |
| JP | 9-512809  | 12/1997 |

* cited by examiner

*Primary Examiner*—Paul A. Zucker
(74) *Attorney, Agent, or Firm*—Oblon, Spivak, McClelland, Maier & Neustadt, P.C.

(57) ABSTRACT

For example, N-[N-(3,3-dimethylbutyl)-L-α-aspartyl]-L-phenylalanine methyl ester (A-type crystal) showing characteristic peaks in diffractive X-ray at diffraction angles (2θ, CuKα ray) of at least 6.0°, 24.8°, 8.2° and 16.5° is dried to its water content below 3% by weight. The crystal thus dried is a novel crystal (C-type crystal) of N-[N-(3,3-dimethylbutyl)-L-α-aspartyl]-L-phenylalanine methyl ester excellent in dissolution rate, and when measured by powder X-ray diffractometry, this crystal shows characteristic peaks in diffractive X-ray at diffraction angles (2θ, CuKα ray) of at least 7.1°, 19.8°, 17.3° and 17.7°. The dissolution rate (solubility) of the C-type crystals is further improved by converting the crystals into granules.

15 Claims, 2 Drawing Sheets

DIFFRACTION STRENGTH

ASPARTAME DERIVATIVE CRYSTAL AND PROCESS FOR PRODUCING THE SAME

This application is a continuation of International Application No. PCT/JP99/02199, filed on Apr. 26, 1999 and claims priority to Japanese Patent Application Serial Nos. 10-125991, filed on May 8, 1998 and 10-207605 filed on Jul. 23, 1998, each of which are incorporated herein by reference in their entirety.

TECHNICAL FIELD

The present invention relates to a novel crystal of a highly sweet substance (sweetener) of N-[N-(3,3-dimethylbutyl)-L-α-aspartyl]-L-phenylalanine methyl ester with improved dissolution rate (solubility), a process for producing the same, and a granule of said crystal excellent in dissolution rate. For reference's sake, as is well-known, L-α-aspartyl-L-phenylalanine methyl ester is a kind of amino acid-based highly sweet sweetener whose commercialization has already been established, and it is abbreviated to "APM" or "Aspartame". Accordingly, the above described sweet substance according to the present invention can be regarded as a derivative of APM or Aspartame, and therefore is abbreviated hereinafter to "N-(3,3-dimethylbutyl)-APM". This sweet substance may be abbreviated to "NM" ("Neotame") in some literatures.

BACKGROUND ART

The efficacy of sweetness of N-(3,3-dimethylbutyl)-APM is at least 50 times as high as that of Aspartame in weight ratio and is about 10,000 times as high as that of sucrose (table sugar), and thus it can constitute a very strong sweetening agent (sweetener).

Because sweeteners are mainly intended for use in foods and consumed by persons, they should be prepared by processes enabling preparing high-purity preparations substantially free from impurities and decomposed materials. To be usable in an industrial scale, such processes should have been established so as to be reproducible at relatively low costs.

The crystal structure of already known N-(3,3-dimethylbutyl)-APM is described as IR spectrum data in WO95/30689. Further, the present inventors analyzed the structure of its single crystal, and as a result, they confirmed that this crystal is a monohydrate, and when measured by powder X-ray diffractometry, the crystal shows characteristic peaks in diffractive X-ray (X-ray diffraction pattern) at diffraction angles (angles of diffraction) at least 6.0°, 24.8°, 8.2°, and 16.5° (2θ, CuKα ray (radiation; line)). For the sake of convenience, the present inventors referred to this crystal as "A-type crystal".

However, the dissolution rate of the A-type crystal in water is low, so there is a commercial and industrial problem in view of the product qualities.

Under the background of such prior art techniques, the problem to be solved by the invention (the object of the present invention) is to provide a novel crystal of a highly sweet sweetener N-(3,3-dimethylbutyl)-APM with improved dissolution rate (solubility), a process for producing the same, and granules of said crystal, improved in solubility.

DISCLOSURE OF INVENTION

As a result of their eager study to solve the above-described problem, the present inventors have found that the water content of dry A-type crystal is usually 3 to 6% (inclusive of water of crystallization), but if this A-type crystal is further dried until its water content is reduced to less than 3%, a novel crystal of N-(3,3-dimethylbutyl)-APM with improved dissolution rate (solubility), from which water of crystallization has been eliminated, is obtained, and also that this novel crystal is granulated (converted into the granules form) whereby its dissolution rate is further improved, and on the basis of these findings, the present invention has been completed. For reference's sake, this novel crystal was referred to as "C-type crystal".

That is, the present invention relates to a novel crystal (C-type crystal) of N-(3,3-dimethylbutyl)-APM, which when measured by powder X-ray diffractometry using CuKα ray (line), shows characteristic peaks in diffractive X-ray at diffraction angles different from those of the A-type crystal, that is, at diffraction angles (2θ) of at least 7.1°, 19.8°, 17.3°, and 17.7°, as well as a process for producing the same, and granules of said novel crystal.

The C-type crystals of the present invention can be obtained for example by drying the A-type crystals until their water content is reduced to less than 3% by weight, as described above.

Many kinds of processes, such as various synthesis processes (methods) are known for the process for producing N-(3,3-dimethylbutyl)-APM, but as a matter of course, the crystal of the present invention can be obtained by not depending on the processes for producing N-(3,3-dimethylbutyl)-APM itself or the kinds thereof.

A dryer (drying equipment) for drying the A-type crystals to obtain the C-type crystals is not limited particularly. Although a through-flow dryer, a fluidized bed dryer, a vacuum dryer, a spray-dryer, a micron dryer, and etc. can be used widely, a vacuum dryer is preferably used.

The production of granules from the C-type crystals as the novel crystals of N-(3,3-dimethylbutyl)-APM made by the present inventors is not particularly limited, and any known and conventionally used granulation process in this field can be suitably used and applied therefor. For example, a dry granulation process or a wet granulation process may be used. Specifically, any method such as mixing granulation, roll press granulation, extrusion granulation, fluidized bed granulation, tumbling granulation, pulverizing granulation, spray-coating, tabletting, and etc. can be used, but the dry granulation method, such as roll press granulation is industrially advantageous for low thermal loading and for easy operation processes without complicated tasks.

For the purpose of easy applications or improvement in quality of sweetness, depending the use applications, the granules of N-(3,3-dimethylbutyl)-APM of the present invention, similar to conventional highly sweet sweetener compositions, can incorporate diluents (thinners) and excipients, such as sugar alcohols, oligosaccharides, food fibers (dietary fibers) and the like, or other highly sweet synthetic sweeteners, such as Alitame, saccharin, and etc., in an amount within such a range as not to spoil the dissolution rate improved by the present invention. The diluents and excipients in this case include sweeteners having a low degree of sweetness, such as sucrose and glucose.

Granulation for a predetermined range of particle diameter can be effected in any method known in the art by subjecting the produced granules to screening and the like.

N-(3,3-dimethylbutyl)-APM is converted into granules having a particle size (diameter) in the range of 100 to 1,400 μm, preferably 100 to 500 μm whereby its dissolution rate (solubility) is further improved, rather than the raw powder form thereof, as is evident, for example, from Test Example 2 below. If the particle size is less than the above range, an action to prevent or suppress (depress) the formation of agglomerates becomes weaker, while with a particle diameter exceeding the above range, its specific surface area becomes smaller, and therefore, the effect of improving dissolution rate is lowered in both the cases.

BEST MODE FOR CARRYING OUT THE INVENTION

Hereinafter, the present invention is described in more detail by reference to Reference Examples and Examples.

Reference Example 1
Preparation of N-(3,3-dimethylbutyl)-APM

The followings were introduced successively under stirring to a reactor equipped with an agitating blade for ensuring very efficient transfer of gaseous hydrogen to a liquid layer. That is, 700 ml of ion exchanged water, 4.21 ml of acetic acid, 20 g of 10% palladium carbon, 1,300 ml of methanol, 56 g of Aspartame and 25 ml of 3,3-dimethylbutylaldehyde were introduced thereinto.

The reactor was filled with a nitrogen gas stream, and the reaction mixture was hydrogenated at a flow rate of 200 ml/min. at room temperature. The progress of this reaction was monitored by sampling the reaction mixture and analyzing the product in high performance liquid chromatography (HPLC). After the hydrogenation reaction for 6 hours, this reaction was terminated by filling the reactor with a nitrogen gas stream and filtering the catalyst through a fine pore filter (0.45 $\mu$m).

As a result of the analysis of the obtained filtrate (1,494 g), the yield was 81%. Subsequently, this filtrate was concentrated to 281 g to remove the methanol, and crystals were precipitated by stirring at 10° C. overnight. Finally, 87 g white wet crystals of N-(3,3-dimethylbutyl)-APM (yield: 77%) were obtained at a high purity (99% or higher, HPLC).

Reference Example 2
Production of A-type Crystals

Figure 1:
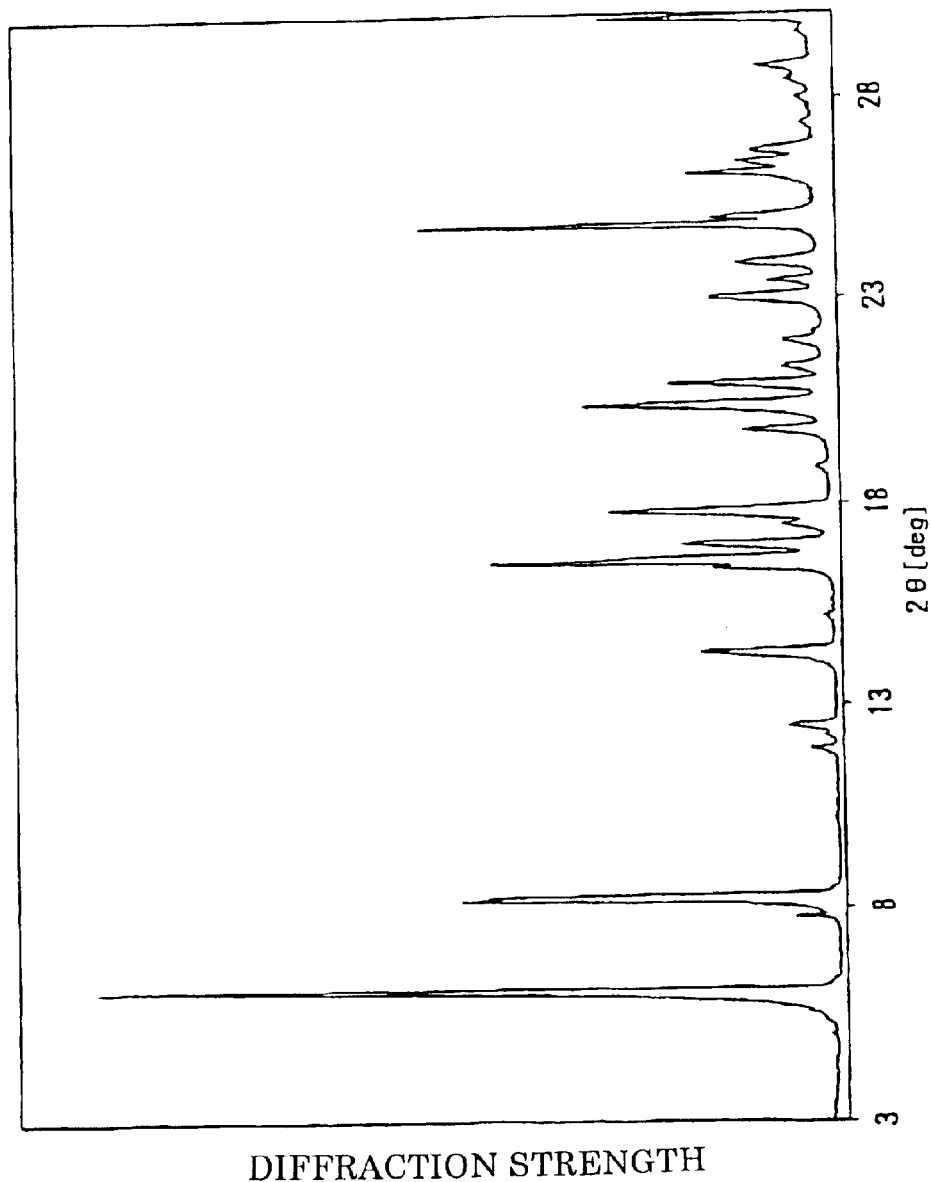
FIG. 1: a powder X-ray diffraction pattern of A-type crystals.

A part of N-(3,3-dimethylbutyl)-APM prepared in Reference Example 1 was used to prepare 100 g aqueous solution of N-(3,3-dimethylbutyl)-APM at a concentration of 3% by weight (dissolved at 60° C.). Then, it was cooled from 60° C. to 30° C. over 5 minutes under stirring. When the liquid temperature reached to 30° C., crystallization of white crystals was initiated. After overnight aging with the liquid temperature kept at 30° C., the crystals were collected by filtration. (a) The diffractive X-ray (X-ray diffraction pattern) of the wet crystals obtained above was measured by powder X-ray diffractometry using CuK$\alpha$ ray (line). The obtained powder X-ray diffraction pattern is shown in FIG. 1.

As is evident from the pattern of the figure, the wet crystals showed characteristic diffraction peaks at least at 6.0°, 24.8°, 8.2°, and 16.5°, indicating that the crystals were A-type crystals.

Further, (b) the wet crystals were placed in a vacuum dryer set at 50° C., and dried until its water content was reduced to 5% by weight. The dried crystals thus obtained were measured by powder X-ray diffractometry using CuK$\alpha$ ray (radiation), indicating that the crystals were A-type crystals as well.

Further, as a result of IR spectrum (KBr) measurement, its values agreed with those described in WO95/30689.

EXAMPLE 1
Production of C-type Crystals

The dried A-type crystals with a water content of 5% by weight described above continued to be dried in the vacuum dryer until their water content was reduced to 0.8% by weight. The average particle size (diameter) of the dried crystals (raw powder) was about 50 $\mu$m.

Figure 2:
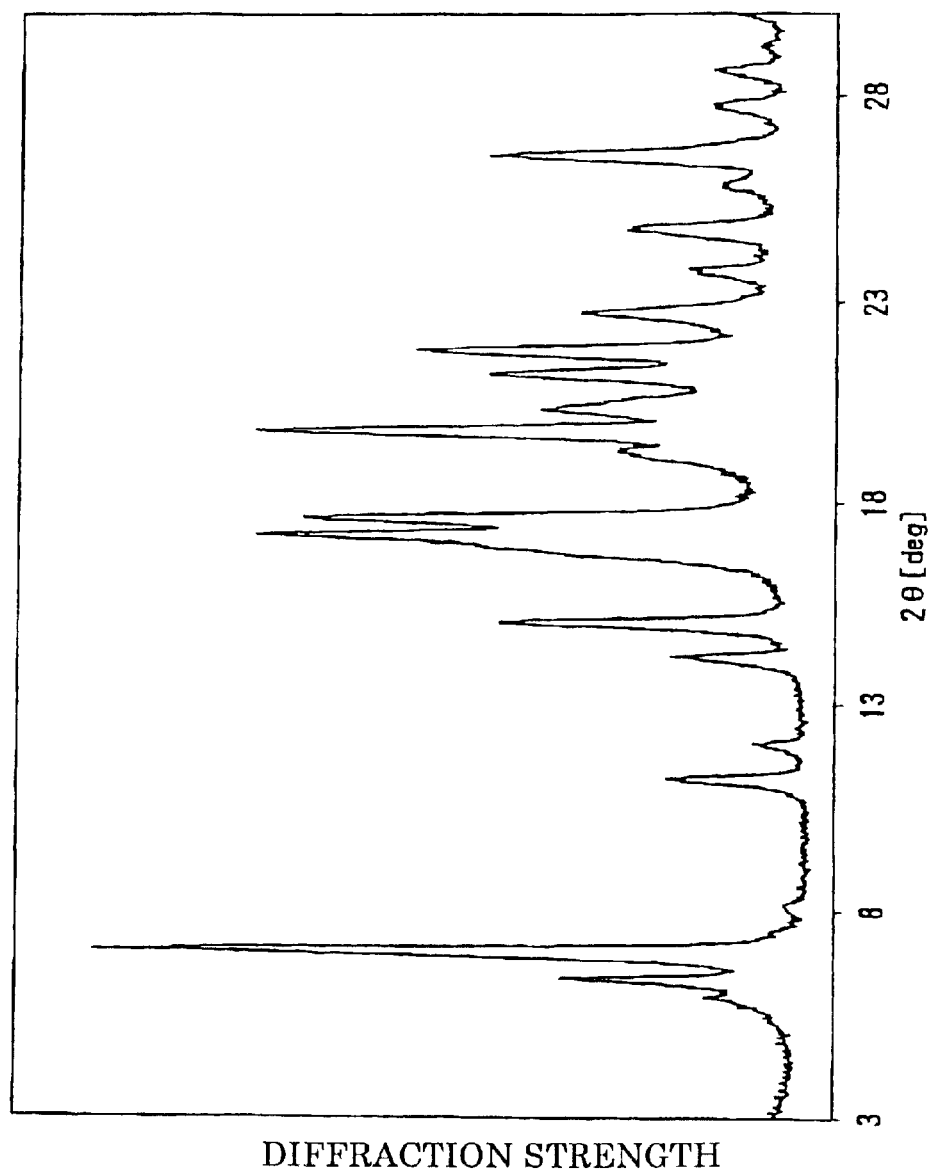
FIG. 2: a powder X-ray diffraction pattern of C-type crystals.

The diffractive X-ray (X-ray diffraction pattern) of the dried crystals was measured by powder X-ray diffractometry using CuK$\alpha$ ray. The obtained powder X-ray diffraction pattern is shown in FIG. 2.

As is evident from the pattern of the figure, the dry crystals showed characteristic diffraction peaks at least at 7.1°, 19.8°, 17.3°, and 17.7°. As described above, the crystals are C-type crystals.

Test Example 1
Measurement of the Dissolution Rate for the Dried Crystals

The dissolution rates of the A-type crystals (Reference Example 2(b)) and the C-type crystals (Example 1) were determined in the following method. That is, 300 mg each of the crystals were introduced into a tabletting mortar (tablet machine) with an internal diameter of 8 mm and a depth of 12 mm, and tabletted at 300 kg/cm2G with "High Pressure Jack J-1 type" (manufactured by Iuchi Seieido) to prepare a sample for measurement of dissolution rate. For measurement of the dissolution rate, the tabletting mortar with only the tabletting face exposed was introduced into 300 ml ion exchanged water kept at 20° C. at a stirring in the number of revolution of 200 rpm, and the inherent dissolution rate was determined using "DISSOLUTION TESTER" (NTR-6100) (manufactured by Toyama Sangyo K. K.).

The result indicated that 17 mg, 34 mg, and 69 mg of the A-type crystals were dissolved for 30 minutes, 60 minutes, and 120 minutes, respectively, whereas 25 mg, 42 mg and 86 mg of the C-type crystals were dissolved for 30 minutes, 60 minutes, and 120 minutes, respectively.

As is evident from the foregoing, the C-type crystals of the present invention were found to be useful crystals with significantly improved dissolution rate, as compared with the A-type crystals.

EXAMPLE 2
Production of Granules of C-type Crystals

The C-type crystals (original (raw) powder with an average particle size (diameter) of 50 $\mu$m) obtained in the same manner as in Example 1 were introduced in an amount of about 300 mg for each operation into a tabletting mortar with an internal diameter of 8 mm and a depth of 12 mm, and subjected to dry compression molding for making tablet at 300 kg/cm2G with "High Pressure Jack J-1 type" (manufactured by Iuchi Seieido), finely divided, and screened to give granule fractions having particle size in the predetermined ranges (100 to 500 $\mu$m and 500 to 1,400 $\mu$m).

Test Example 2
Measurement of the Dissolution Rates of the C-type Crystals (Original Powder) and Granules Thereof 0.5 g of the sample was introduced into 900 ml water (20° C.) in a 1-L elution tester (the Japanese Pharmacopoeia, Paddle method, 100 rpm) and its dissolution time was measured (end point was visually confirmed).

That is, the C-type crystals (original powder with an average particle size of about 50 μm) obtained in Example 1 above and the granules (particle size of 100 to 500 μm and 500 to 1,400 μm) of C-type crystals obtained in Example 2 above were examined for measurements of their dissolution times in the same manner as described above.

The results indicated that the dissolution time of the original (raw) powder was 55 minutes, whereas the dissolution times of the granules were only 16 minutes for particle size (diameter) of 100 to 500 μm and only 37 minutes for particle size of 500 to 1,400 μm.

As can be seen from the results of Test Examples 1 and 2, the dissolution rate (solubility) of N-(3,3-dimethylbutyl)-APM which is a highly sweet synthetic sweetener, is improved by converting the A-type crystals under heating into the C-type crystals, and further the dissolution rate of the C-type crystals is further improved by granulating them.

What is claimed is:

1. A crystal of N-[N-(3,3-dimethylbutyl)-L-α-aspartyl]-L-phenylalanine methyl ester showing a characteristic X-ray diffraction peak at a diffraction angle (2θ, CuKα ray) of about 7.1°.

2. A process for producing the crystal according to claim 1, which comprises drying N-[N-(3,3-dimethylbutyl)-L-α-aspartyl]-L-phenylalanine methyl ester showing a characteristic X-ray diffraction peak at a diffraction angle (2θ, CuKα ray) of about 6.0° until its water content is reduced to less than 3% by weight.

3. A granule of the crystal of N-[N-(3,3-dimethylbutyl)-L-α-aspartyl]-L-phenylalanine methyl ester according to claim 1, having a particle size ranging from 100 to 1,400 μm.

4. A granule according to claim 3 having a particle size ranging from 100 to 500 μm.

5. A food sweetener composition comprising a granule of N-[N-(3,3-dimethylbutyl)-L-α-aspartyl]-L-phenylalanine methyl ester according to claim 3, and at least one other ingredient.

6. A composition according to claim 5 wherein the other ingredient is a diluent or excipient.

7. A composition according to claim 6 wherein the diluent or excipient is selected from the group consisting of a natural sweetener, a synthetic sweetener, a sugar alcohol, an oligosaccharide, food fibers and mixtures thereof.

8. A composition according to claim 7 wherein the natural sweetener is glucose.

9. A composition according to claim 7 wherein the natural sweetener is sucrose.

10. A composition according to claim 7 wherein the synthetic sweetener is saccharin.

11. A composition according to claim 5 which is in the form of a food product.

12. A composition according to claim 11 wherein the food product is a table sweetener.

13. A composition according to claim 11 wherein the food product is a beverage.

14. A C-type crystal of N-[N-(3,3-dimethylbutyl)-L-α-aspartyl]-L-phenylalanine methyl ester.

15. A granule of the C-type crystal of claim 14 having a particle size ranging from 100 to 1,400 μm.

* * * * *